US 11,625,927 B2

(12) United States Patent
Morimoto et al.

(10) Patent No.: US 11,625,927 B2
(45) Date of Patent: Apr. 11, 2023

(54) ABNORMALITY DETERMINATION APPARATUS (71) Applicant: DENSO CORPORATION, Kariya (JP)

(72) Inventors: Hiroshi Morimoto, Kariya (JP); Yukiyasu Yoshimura, Kariya (JP)

(73) Assignee: DENSO CORPORATION, Kariya (JP)

(*) Notice: Subject to any disclaimer, the term of this patent is extended or adjusted under 35 U.S.C. 154(b) by 178 days.

(21) Appl. No.: 17/142,765

(22) Filed: Jan. 6, 2021

(65) Prior Publication Data
US 2021/0124963 A1 Apr. 29, 2021

Related U.S. Application Data (63) Continuation of application No. PCT/JP2019/026326, filed on Jul. 2, 2019.

(30) Foreign Application Priority Data

Jul. 9, 2018 (JP) .............................. JP2018-130005

(51) Int. Cl.
G06V 20/59 (2022.01)
G06V 40/16 (2022.01)

(52) U.S. Cl.
CPC ............ G06V 20/597 (2022.01); G06V 40/16 (2022.01)

(58) Field of Classification Search
CPC ...... G06V 20/597; G06V 40/16; G06V 10/40; A61B 5/11; A61B 5/18; B60R 11/04; B60R 16/02; B60W 40/08; G06T 7/00; G08B 21/00; G08B 21/02; G08G 1/16
See application file for complete search history.

(56) References Cited

U.S. PATENT DOCUMENTS

| 9,491,374 | B1* | 11/2016 | Avrahami | H04N 7/147 |
| 10,275,670 | B1* | 4/2019 | Li | G06V 40/16 |
| 10,949,688 | B2* | 3/2021 | Katsumata | G06V 20/64 |
| 11,422,352 | B2* | 8/2022 | Quarre | G02B 21/26 |
| 2006/0261931 | A1 | 11/2006 | Cheng | |
| 2013/0018549 | A1 | 1/2013 | Kobana et al. | |
| 2014/0293053 | A1* | 10/2014 | Chuang | B60K 28/066 348/148 |
| 2016/0150065 | A1* | 5/2016 | Waltermann | H04M 3/42382 455/569.1 |
| 2017/0332044 | A1* | 11/2017 | Marlow | G06V 20/46 |
| 2018/0014754 | A1* | 1/2018 | Gray | A61B 5/1116 |

(Continued)

FOREIGN PATENT DOCUMENTS

| JP | 2005108033 A | 4/2005 |
| JP | 2016085563 A | 5/2016 |
| WO | WO-2013008299 A1 | 1/2013 |

Primary Examiner — Ming Y Hon
(74) Attorney, Agent, or Firm — Harness, Dickey & Pierce, P.L.C.

(57) ABSTRACT

An abnormality determination apparatus is mounted on a vehicle. A person is identified in a captured image acquired from a camera that captures a range including a driver seat of the vehicle. It is determined whether a person other than the driver of the vehicle is present in an operable range set as a range in which a steering wheel of the vehicle is enabled to be operated, based on a result from identifying a person. An abnormality process assuming that the driver of the vehicle is in an abnormal state is executed in response to determining that the person other than the driver is present in the operable range.

12 Claims, 5 Drawing Sheets (56) References Cited

U.S. PATENT DOCUMENTS

| | | | |
|---|---|---|---|
| 2018/0118219 A1* | 5/2018 | Hiei | B60W 40/09 |
| 2019/0016188 A1* | 1/2019 | Hachisuka | B60G 17/0164 |
| 2019/0046080 A1* | 2/2019 | Nishikado | A61B 5/0077 |
| 2019/0215464 A1* | 7/2019 | Kumar | H04N 7/08 |
| 2021/0291837 A1* | 9/2021 | Aizawa | G08G 1/09623 |
| 2022/0019059 A1* | 1/2022 | Kamebuchi | G02B 27/0025 |
| 2022/0239848 A1* | 7/2022 | Swierk | G06T 5/002 |

* cited by examiner

ABNORMALITY DETERMINATION APPARATUS

CROSS REFERENCE TO RELATED APPLICATIONS

The present application is a continuation application of International Patent Application No. PCT/JP2019/026326 filed on Jul. 2, 2019, which designated the U.S. and claims the benefit of priority from Japanese Patent Application No. 2018-130005 filed on Jul. 9, 2018. The entire disclosures of all of the above applications are incorporated herein by reference.

TECHNICAL FIELD

The present disclosure relates to an abnormality determination apparatus.

BACKGROUND

There is a vehicle control apparatus that executes appropriate processing for safety when the vehicle driver is in an abnormal state that interferes with driving. The vehicle control apparatus determines whether the driver is in a drowsiness state or an inoperable state based on the driver's state monitoring information and the driver's face information detected in the captured image by the camera. If it is determined that the driver is in a drowsiness state or an inoperable state, the vehicle control such as deceleration and stop is executed.

SUMMARY

According to an example of the present disclosure, an abnormality determination apparatus is mounted on a vehicle. A person is identified in a captured image acquired from a camera that captures a range including a driver seat of the vehicle. It is determined whether a person other than the driver of the vehicle is present in an operable range set as a range in which a steering wheel of the vehicle is enabled to be operated, based on a result from identifying a person. An abnormality process assuming that the driver of the vehicle is in an abnormal state is executed in response to determining that the person other than the driver is present in the operable range.

BRIEF DESCRIPTION OF DRAWINGS

The objects, features, and advantages of the present disclosure will become more apparent from the following detailed description made with reference to the accompanying drawings. In the drawings.

DETAILED DESCRIPTION

Exemplary embodiments of the present disclosure will be described below with reference to the drawings.

1. First Embodiment

1-1. Configuration

Figure 1:
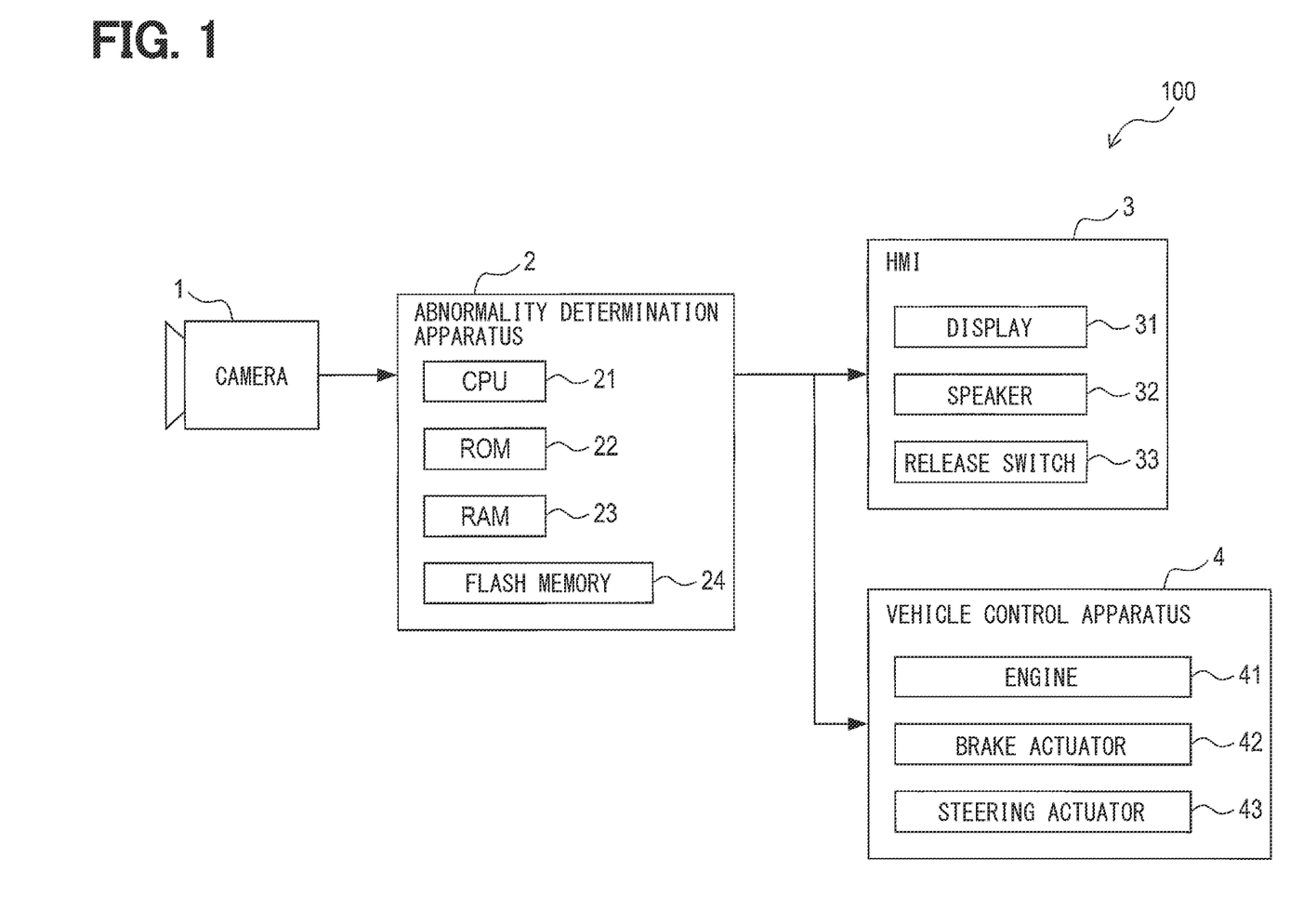
FIG. 1 is a block diagram illustrating a configuration of an abnormality determination system.

An abnormality determination system 100 shown in FIG. 1 is a system installed in a vehicle such as a bus that carries a large number of passengers; the abnormality determination system 100 includes cameras 1, an HMI (Human Machine Interface) 3, a vehicle control apparatus 4, and an abnormality determination apparatus 2, which is connected with the cameras 1, the HMI 3, and the vehicle control apparatus 4 via a communication link.

Each camera 1 is an imager capable of capturing an image of a range including a driver seat of a vehicle; the cameras 1 are arranged, for example, at a plurality of respective positions in front of a driver of the vehicle. The camera 1 outputs a signal representing a captured image to the abnormality determination apparatus 2. Based on the captured image acquired from the camera 1, the abnormality determination apparatus 2 can specify the three-dimensional position of a person or the like included in the captured image.

As one example of the present disclosure, the abnormality determination apparatus 2 may mainly include a well-known microcomputer having a CPU 21, a ROM 22, a RAM 23, a flash memory 24, and the like. The CPU 21 executes the program stored in the ROM 22, which is a non-transitory tangible storage medium. By executing this program, a method corresponding to the program is executed. Specifically, the abnormality determination apparatus 2 executes an abnormality determination process shown in FIG. 2 described later according to the program. The abnormality determination apparatus 2 outputs a signal representing the result of the abnormality determination process to the HMI 3 and the vehicle control apparatus 4. The abnormality determination apparatus 2 may include one microcomputer, or may include a plurality of microcomputers. In addition, the method of executing each function of the abnormality determination apparatus 2 is not limited to software, and a part or all of its functions may be executed by using one or more hardware circuits. For example, when the above-described functions may be implemented by an electronic circuit which is hardware, the electronic circuit may be implemented by a digital circuit, an analog circuit, or a combination thereof.

In other words, the abnormality determination apparatus 2 may be configured to be or include one or more than one electronic controller circuit providing a plurality of functions or units which will be described later. Such an electronic controller circuit or an individual function or unit provided by the electronic controller circuit may be implemented (i) by configuring a central processing unit (CPU) and a memory storing a computer program executed by the CPU, or (ii) by configuring one or more special purpose hardware logic circuits and/or analog circuits without any CPU, or (iii) by configuring a combination of (a) the CPU and the memory and (b) the one or more hardware logic circuits and/or analog circuits.

The HMI 3 includes a display 31, a speaker 32, and a release switch 33.

The display 31 is an in-vehicle display that displays an image, and is provided at a position where a driver of the vehicle can visually recognize it.

The speaker 32 is an in-vehicle speaker shared with a car navigation device, an audio device, and the like.

The release switch 33 is a switch provided in a range in which the driver of the vehicle can operate, and can stop the notification of the abnormal state of the driver. That is, as will be described later, in the present embodiment, when it is determined that the driver is in an abnormal state, the abnormal state of the driver is notified. However, even though the driver is in a normal state, there is may be a case where the driver's posture is determined to be abnormal due to the driver's posture being collapsed when trying to pick up an object near the driver seat. In such a case, an abnormal state of the driver is notified of. Therefore, the abnormality determination system 100 is configured to stop the notification by pressing the release switch 33.

The vehicle control apparatus 4 includes an engine 41, a brake actuator 42, and a steering actuator 43. The vehicle control apparatus 4 safely and automatically stops the vehicle when it is determined by the abnormality determination process described later that the driver is in an abnormal state. Specifically, the vehicle control apparatus 4 decelerates or stops the vehicle by controlling the engine 41 or the brake actuator 42 in the vehicle, for example. Further, the vehicle control apparatus 4 retracts the vehicle to the road shoulder by also performing steering angle control of steering by the steering actuator 43, for example.

1-2. Process

Figure 2:
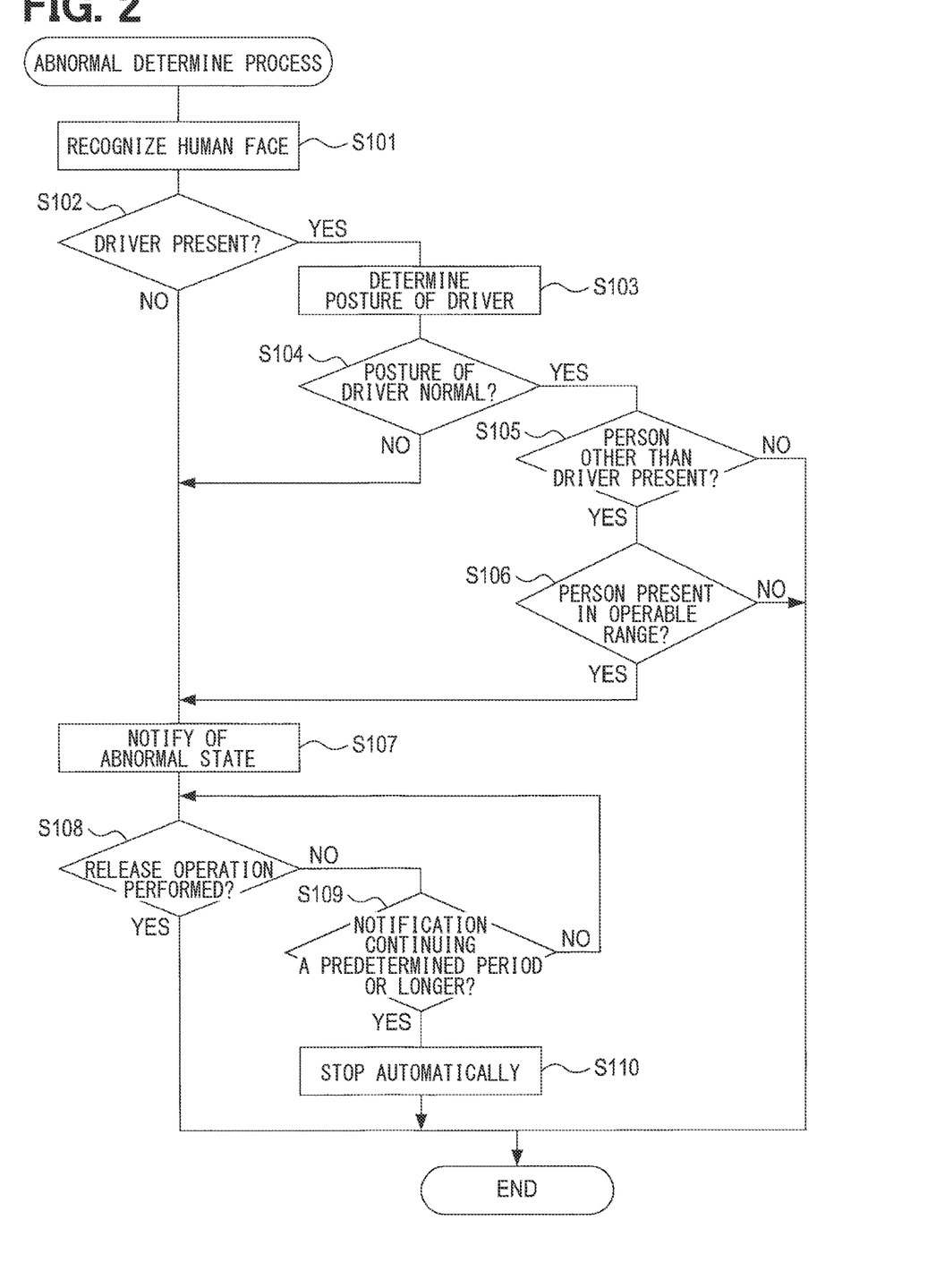
FIG. 2 is a flowchart of an abnormality determination process according to a first embodiment.

Next, the abnormality determination process executed by the abnormality determination apparatus 2 will be described with reference to the flowchart of FIG. 2. This abnormality determination process is periodically executed while the ignition switch is tuned on.

First, in S101, the abnormality determination apparatus 2 identifies a person by analyzing a captured image acquired from the camera 1. In this embodiment, a person is identified in the captured image using a well-known pattern matching method. Further, in S101, the abnormality determination apparatus 2 further recognizes a human face of the identified person by analyzing the captured image. In this embodiment, a human face is recognized based on the relative positions of facial feature points such as eyes and nose specified in the captured image.

Then, in S102, the abnormality determination apparatus 2 determines whether the driver is present in the captured image based on the identification result in S101. Specifically, the abnormality determination apparatus 2 determines whether the driver is present in the captured image based on the recognition result. In the present embodiment, the driver's face feature point information registered in advance in the flash memory 24 is compared with the person's face feature point information recognized in the captured image to identify the driver. That is, the information on the facial feature points of the driver registered in advance and the information on the facial feature points of the recognized person are compared to determine whether the both correspond to the same person. When it is determined that the both correspond to the same person, it is determined that the driver is present in the captured image. When the abnormality determination apparatus 2 determines in S102 that the driver is not present in the captured image, the process proceeds to S107, which will be described later. That is, if the driver is not present in the captured image, it means that the driver is not present in the driver seat. It is therefore determined that the driver is in an abnormal state.

On the other hand, when the abnormality determination apparatus 2 determines in S102 that the driver is present in the captured image, the process proceeds to S103.

In S103, the abnormality determination apparatus 2 determines the posture of the driver in the captured image. The posture of the driver is determined by detecting the inclination of the head with respect to the body based on the identification result in S101.

Subsequently, in S104, the abnormality determination apparatus 2 determines whether the posture of the driver is normal. In the present embodiment, when an inclination of the head of the driver with respect to the body is equal to or greater than a predetermined threshold and such an inclination continues for a predetermined period of time, it is determined that the driver's posture is not normal. If the abnormality determination apparatus 2 determines in S104 that the driver's posture is not normal, the abnormality determination apparatus 2 moves the process to S107, which will be described later. In other words, when the driver's posture is not normal, for example, when the driver is faint and the head is tilted, it is determined that the driver is in an abnormal state.

On the other hand, when the abnormality determination apparatus 2 determines in S104 that the driver's posture is normal, the process proceeds to S105.

In S105, the abnormality determination apparatus 2 determines whether a person other than the driver is present in the captured image based on the recognition result in S101. In the present embodiment, when a person other than the person identified as the driver in the captured image is identified in S101, it is determined that the person other than the driver is present. If the abnormality determination apparatus 2 determines in S105 that no person other than the driver is present in the captured image, the process returns to S101.

On the other hand, if the abnormality determination apparatus 2 determines in S105 that a person other than the driver is present in the captured image, the process proceeds to S106.

Figure 3:
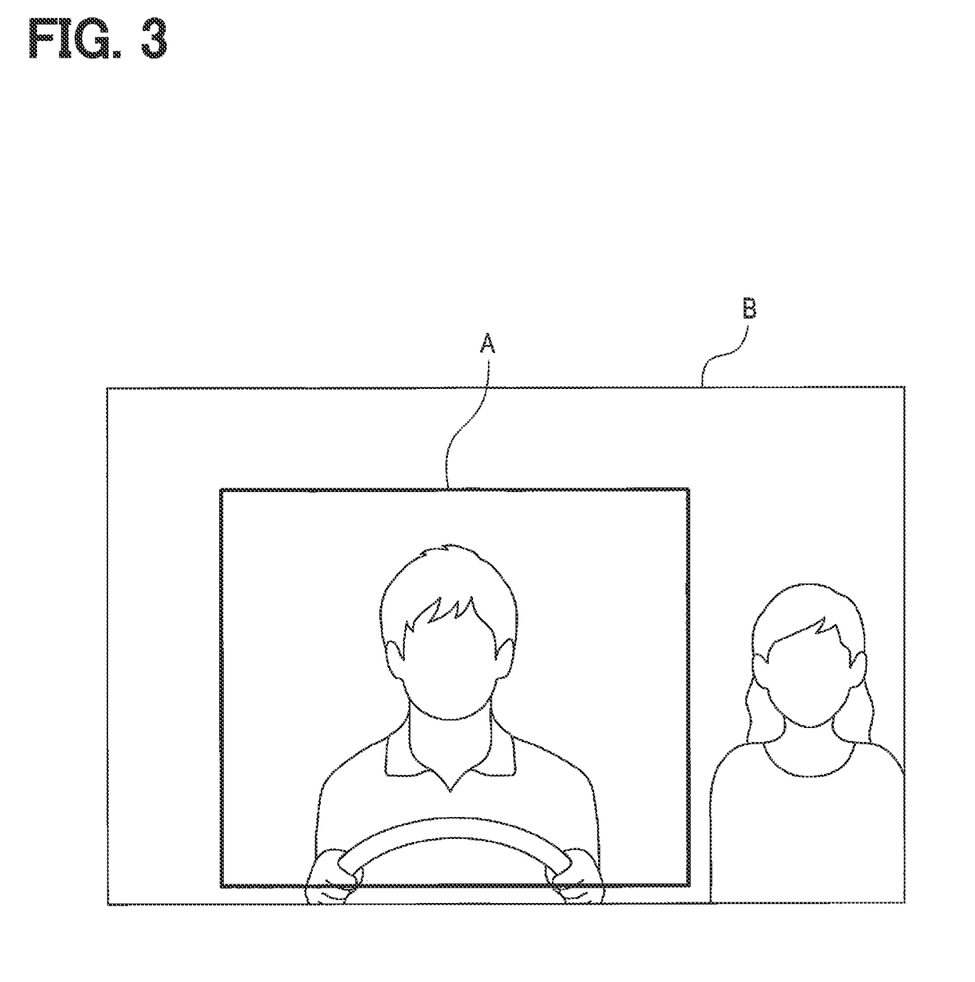
FIG. 3 is a diagram illustrating a setting range set around a steering wheel in a two-dimensional captured image.

In S106, the abnormality determination apparatus 2 determines whether a person other than the driver is present in an operable range preset as a range in which the steering wheel of the vehicle is enabled to be operated. The operable range is, for example, a range in which the driver can operate the steering wheel in order to drive the vehicle. In the present embodiment, as shown in FIG. 3, the setting range A is set around the steering wheel in the two-dimensional captured image B. In the present embodiment, if a person other than the driver determined to be present in S105 is not present in the setting range A in the captured image B, it is determined that no person other than the driver is present in the operable range. If it is determined in S106 that no person other than the driver is present in the operable range, the abnormality determination apparatus 2 returns the process to S101. That is, if the driver is determined to be in a normal state and a passenger is not near the steering wheel, it is determined that the driver is not in an abnormal state.

On the other hand, when the abnormality determination apparatus 2 determines in S106 that a person other than the driver is present in the operable range, the abnormality determination apparatus 2 advances the process to S107. That is, even in cases that the driver is determined to have been in a normal state, if a person other than the driver is present in the setting range A, it is highly possible that a passenger present near the steering wheel is intervening in driving the vehicle. Therefore, it is determined that the driver is in an abnormal state.

In S107, the abnormality determination apparatus 2 determines that the driver is in an abnormal state, and therefore notifies the vehicle driver of the abnormal state. In the present embodiment, the display 31 is used to display an image for notifying of the abnormal state of the driver, and the speaker 32 is used for notifying by sounds or the like of the abnormal state of the driver. Note that the abnormality determination apparatus 2 executes S107 as the abnormality process.

Subsequently, in S108, the abnormality determination apparatus 2 determines whether the release operation has been executed. In the present embodiment, whether the release operation has been performed is determined by whether the release switch 33 is pressed by the driver. When the release switch 33 is pressed, it is determined that the release operation has been performed. If the abnormality determination apparatus 2 determines in S108 that the release operation has not been performed, the process proceeds to S109.

In S109, the abnormality determination apparatus 2 determines whether the notification state for notifying that the driver is in an abnormal state has continued for a predetermined period of time or longer. If the abnormality determination apparatus 2 determines in S109 that the notification state has not continued for a predetermined period of time or longer, the process returns to S108.

If it is determined in S108 that the release operation has been performed, the abnormality determination apparatus 2 returns the process to S101. That is, even in cases that the driver is notified of an abnormal state, if the driver performs the release operation within a predetermined period of time, it is determined that the driver is not in an abnormal state.

On the other hand, when the abnormality determination apparatus 2 determines in S109 that the notification state has continued for the predetermined period of time or longer, the process proceeds to S110.

In S110, the abnormality determination apparatus 2 executes the control for automatically stopping the vehicle by the vehicle control apparatus 4 described above. The abnormality determination apparatus 2 executes S110 as the abnormality process. After that, the abnormality determination apparatus 2 ends the abnormality determination process of FIG. 2.

1-3. Effects

According to the first embodiment described above, the following effects are obtained.

(1a) According to this embodiment, it is possible to detect an abnormal state of the driver that cannot be detected by the information of the driver alone.

Figure 4:
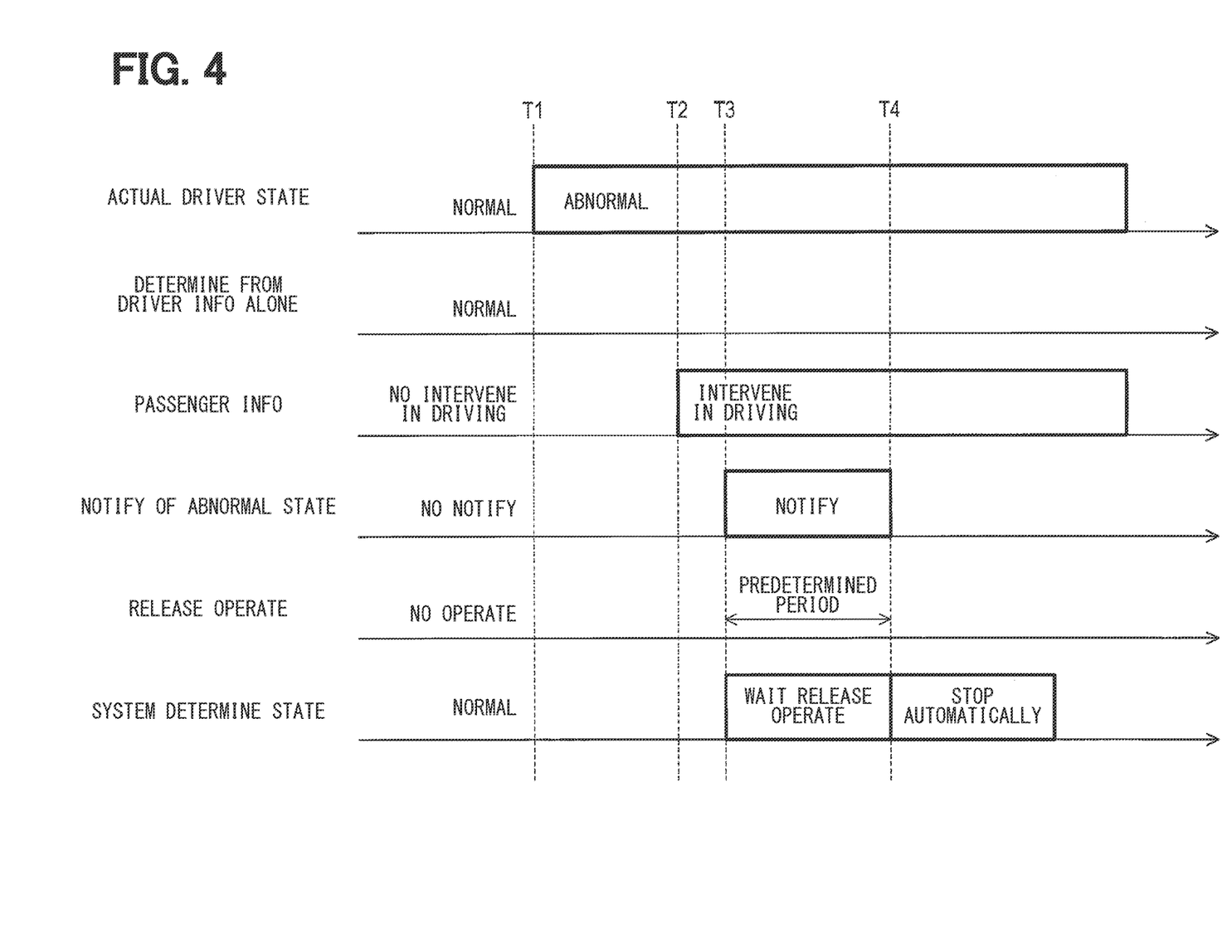
FIG. 4 is a timing chart illustrating an example that determines that the driver is in an abnormal state.

Here, an example of a specific situation in which the driver is determined to be in an abnormal state in the present embodiment will be described using the timing chart of FIG. 4.

At time T1, the driver becomes abnormal without losing their posture. In this case, it is conceivable that the posture of the driver is determined to be normal, and the driver is not determined to be in an abnormal state. However, at time T2, when a passenger who has sensed an abnormal state of the driver intervenes in driving, a person other than the driver is present in the setting range A. Therefore, it is determined that a person other than the driver is present in the operable range, and the driver is determined to be in an abnormal state. Then, at time T3, the abnormal state of the driver is notified. After that, when the notification state continues for a predetermined period of time or longer without the driver performing the releasing operation, the control for automatically stopping the vehicle is executed at time T4.

As described above, when it is determined whether the driver is in the abnormal state based on the information on the driver only, the driver may be erroneously determined to be in the normal state. On the other hand, the configuration of the present embodiment determines whether the driver is in an abnormal state in consideration of the information of the person other than the driver. According to this, it is possible to automatically stop the vehicle by detecting an abnormal state of the driver that cannot be detected by the information of the driver alone.

(1b) In the present embodiment, it is determined whether the notification state has continued for a predetermined period of time or longer. Then, even in cases that the driver is notified of the abnormal state, if the driver performs the release operation within a predetermined period of time, the notification is stopped. Therefore, it is possible to prevent the control for automatically stopping the vehicle from being executed even when the abnormal state of the driver is notified of although the driver is normal.

In the first embodiment, S101 corresponds to the process as an identification unit; S102 and S106 correspond to the process as a person determination unit; and S107 and S110 correspond to the process as an abnormality processing unit.

2. Second Embodiment 2-1. Configuration

Since the abnormality determination system of a second embodiment has the same basic configuration as that of the first embodiment, the same components as those of the first embodiment will be designated by the same reference numerals and description thereof will be omitted.

2-2. Process

Figure 5:
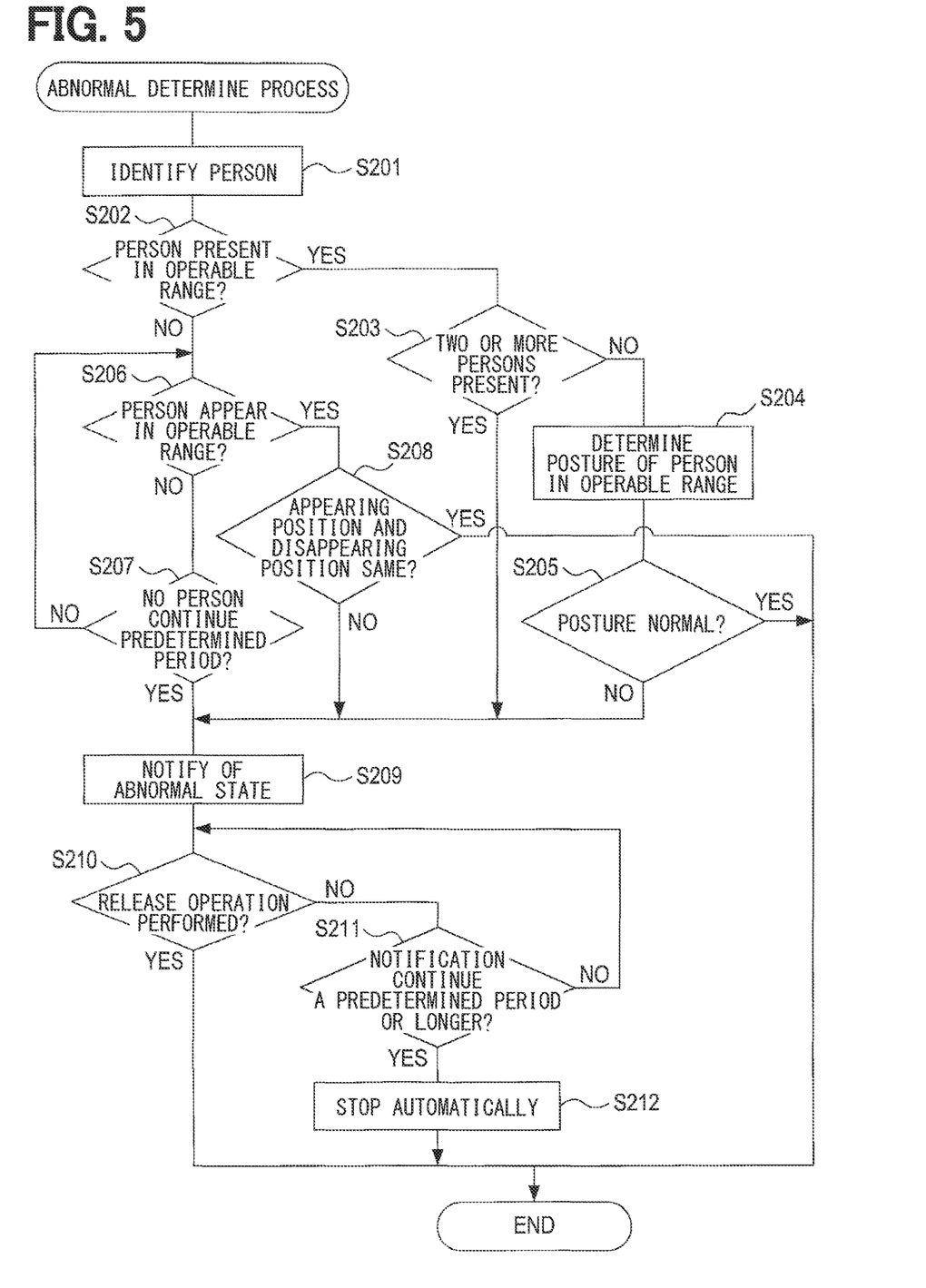
FIG. 5 is a flowchart of an abnormality determination process according to a second embodiment.

Next, the abnormality determination process executed by the abnormality determination apparatus 2 will be described with reference to the flowchart of FIG. 5. Note that the processing of S209 to S212 in FIG. 5 is the same as the processing of S107 to S110 in FIG. 2.

In S201, the abnormality determination apparatus 2 identifies a person by analyzing a captured image acquired from the camera 1. In the present embodiment, unlike the first embodiment, recognition of the face of the identified person is not required.

In S202, the abnormality determination apparatus 2 determines whether a person is present in the operable range based on the identification result in S201. In S202, when the person identified in S201 is present in the setting range A, it is determined that a person is present in the operable range, as in S106 of the first embodiment. If the abnormality determination apparatus 2 determines in S202 that a person is present in the operable range, the process proceeds to S203.

In S203, the abnormality determination apparatus 2 determines whether two or more persons are present in the operable range. If it is determined in S203 that two or more persons are present in the operable range, the abnormality determination apparatus 2 advances the process to S209. That is, when two or more persons are present in the setting range A, the persons, who are assumed to be the driver and a passenger who is a person other than the driver near the steering wheel, likely to intervene in driving the vehicle. Therefore, it is determined that the driver is in an abnormal state.

On the other hand, if the abnormality determination apparatus 2 determines in S203 that more than two persons are not present in the operable range, that is, if there is one person who is assumed to be the driver in the operable range, the abnormality determination apparatus 2 advances the process to S204.

In S204, the abnormality determination apparatus 2 determines the posture of the person present in the operable range. The determination method in S204 is the same as the processing in S103 of the first embodiment.

Subsequently, in S205, the abnormality determination apparatus 2 determines whether the posture of the person present in the operable range is normal. The determination method in S205 is the same as the processing in S104 of the first embodiment. If the abnormality determination apparatus 2 determines in S205 that the posture of the person present in the operable range is normal, the abnormality determination apparatus 2 returns the process to S201. That is, if the person assumed to be the driver is determined to be in a normal state and the passenger is not near the steering wheel, it is determined that the driver is not in an abnormal state.

On the other hand, when the abnormality determination apparatus 2 determines in S205 that the posture of the person existing in the operable range is not normal, the abnormality determination apparatus 2 advances the process to S209. In other words, if the posture of the person assumed to be the driver is not normal, for example, if the person assumed to be the driver loses his/her head and leans, the driver is determined to be in an abnormal state.

On the other hand, when the abnormality determination apparatus 2 determines in S202 that no person is present in the operable range, the process proceeds to S206. In other words, if there is no person in the operable range, the following cases are possible. That is, there is a possibility that the driver has lost their mind and has disappeared from the operable range, or there is a possibility that a driver who intentionally disappears from the operable range due to picking up an object near the driver seat may return to the imageable range. Therefore, it is determined whether the driver is in an abnormal state in the subsequent processing of S206 to S208.

In S206, the abnormality determination apparatus 2 determines whether a person has appeared in the operable range. In the present embodiment, when a person is present in the setting range A, it is determined that a person appears in the operable range. If the abnormality determination apparatus 2 determines in S206 that no person appears in the operable range, the process proceeds to S207.

In S207, the abnormality determination apparatus 2 determines whether the absence state in which no person appears in the operable range has continued for a predetermined period of time or longer. In the present embodiment, it is determined whether the absence state has continued for three (3) seconds or longer. If the abnormality determination apparatus 2 determines in S207 that the absence state has continued for a predetermined period of time or longer, the process proceeds to S209. That is, there is a possibility that the driver's disappearing from the operable range is not due to the intended action, and thus it is determined that the driver is in an abnormal state.

On the other hand, when the abnormality determination apparatus 2 determines in S207 that the absence state has not continued for the predetermined period of time or longer, the process returns to S206. That is, when the absence state in the operable range of the driver is less than 3 seconds, it is too early to determine that the driver is in an abnormal state, so the driver is not determined to be in an abnormal state.

On the other hand, when the abnormality determination apparatus 2 determines in S206 that a person appears in the operable range, the process proceeds to S208.

In S208, the abnormality determination apparatus 2 determines whether (i) an appearing position that is a position via which a person appears into the operable range, and (ii) a disappearing position that is a position via which a person disappears from the operable range, are the same. Specifically, the abnormality determination apparatus 2 determines whether an appearing position via which a person appears into the operable range in the current cycle is the same as a disappearing position via which a person disappears from the operable range in the previous cycle, which is stored in the flash memory 24, before the current cycle. Here, when there are a plurality of disappearing positions, the disappearing position used for the above determination is the latest disappearing position, that is, immediately before the appearance of the appearing person at the appearing position in the current cycle. Then, the abnormality determination apparatus 2 determines whether the appearing person and the disappearing person are the same person by determining whether the appearing position and the disappearing position are the same.

In the present embodiment, each of the appearing position and the disappearing position in the operable range is classified into one of two left and right positions with respect to the driver seat. As described below, it is determined whether the appearing person and the disappearing person are the same person.

First, the following will describe an example case where the appearing position and the disappearing position are different. For example, the appearing position is on the left side of the driver seat, and the disappearing position is on the right side of the driver seat. In such a case, the driver may lose consciousness and disappear to the right side of the driver seat; then, the passenger who intervenes in driving after detecting the abnormal condition of the driver may appear from the left side of the driver seat. In this case, the driver is the disappearing person and the passenger is the appearing person. Further, it is unlikely that the driver disappears to the right side of the driver seat and appears from the left side of the driver seat. Therefore, when the appearing position and the disappearing position are different, it is considered that the disappearing person is the driver and the appearing person is the passenger. It is thus determined that the appearing person and the disappearing person are not the same person.

The following will describe an example case where the appearing position and the disappearing position are the same, for example, the appearing position is on the left side of the driver seat and the disappearing position is on the left side of the driver seat. In such a case, the following situation is conceivable. That is, a person assumed to be a driver temporarily disappears to the right side of the driver seat by, for example, intentionally bending down, but then returns to the original posture to appear from the right side of the driver seat after completing the intended action. For example, it is conceivable that the driver bent over to pick up an object near the driver seat and disappeared from the operable range, but picked up the object and returned. Therefore, when the appearing position and the disappearing position are the same, the disappearing person and the appearing person are highly likely to be driver, and thus the appearing person and the disappearing person are determined to be the same person.

When the abnormality determination apparatus 2 determines in S208 that the appearing position and the disappearing position are not the same, the process proceeds to S209. That is, when the appearing person and the disappearing person are not the same person, it is determined that the driver is in an abnormal state.

On the other hand, when the abnormality determination apparatus 2 determines in S208 that the appearing position and the disappearing position are the same, the process returns to S201. That is, since it is highly possible that the appearing person and the disappearing person are the same person, it is determined that the driver is not in an abnormal state.

2-3. Effects

According to the second embodiment described in detail above, the following effects can be obtained in addition to the effects (1a) and (1b) of the first embodiment described above.

(2a) In this embodiment, when it is determined that the driver is in an abnormal state based on the appearing position and the disappearing position, the abnormal state of the driver is notified. That is, based on the appearing position and the disappearing position, it is determined whether the appearing person and the disappearing person are the same person. Thus, it is possible to determine whether the driver is in an abnormal state by determining whether the appearing person and the disappearing person are the same person without identifying the driver by using face recognition.

(2b) In this embodiment, if a person appears in the operable range within a predetermined period of time after the person disappears from the operable range, it is not determined that the driver is in an abnormal state. For example, suppose a case where a driver who intentionally disappears from the operable range due to picking up an object near the driver seat and then returns to the imageable range within a predetermined period of time. Even in such a case, the configuration according to the second embodiment can prevent the driver from being erroneously determined to be in an abnormal state. In addition, in the present embodiment, if the person does not appear in the operable range even after a lapse of a predetermined period of time after the person disappears from the operable range, it is determined that the driver is in an abnormal state. Therefore, for example, when (i) the driver loses their mind and disappears from the operable range, and (ii) there is no passenger who intervenes in driving by detecting the abnormal state of the driver, it may be determined that the driver is in an abnormal state.

In the second embodiment, S201 corresponds to the process as an identification unit, S202 corresponds to the process as a presence determination unit, S203 corresponds to the process as a person determination unit, and S209 and S212 correspond to the process as an abnormality processing unit.

3. Other Embodiments

While the embodiment of the present disclosure has been described above, the present disclosure is not limited to the above embodiment and can be variously modified.

(3a) In the first embodiment, an example configuration is illustrated in which the driver is identified by comparing the information of the facial feature points of the driver registered in advance and the information of the facial feature points of the recognized person has been exemplified. The face recognition method for identifying the driver is not limited to this. For example, when the ignition switch is turned on, information on the feature points of the face of the person sitting in the driver seat may be stored as driver information for comparison. In addition, even if the driver is identified by comparing the information on the feature points of the human face acquired in the previous cycle before the current cycle and the information of the feature points of the human face acquired in the current cycle.

(3b) In the second embodiment described above, an example configuration is illustrated in which each of the appearing position and the disappearing position in the operable range is classified into one of two left and right positions with respect to the driver seat. The classification method thereof is not limited to this. For example, it may be classified into any one of four positions in the left, the right, the top, and the bottom. In such a case, for example, when the appearing position is the top left side of the driver seat and the disappearing position is any one of the bottom right side, the top right side, and the bottom left side of the driver seat, the appearing position and the disappearing position may be determined to be not the same. That is, not only when the left and right positions of the appearing position and the disappearing position are different, but even when the left and right positions are the same but the top and bottom positions are different, it is may be determined that the appearing position and the disappearing position are not the same.

(3c) The setting range may be a setting range set in the three-dimensional space. That is, in each of the above embodiments, the rectangular range in the captured image is set as the setting range A. However, there is no need to be limited thereto. For example, a rectangular parallelepiped range in which the setting range A in each of the above-described embodiments has a certain depth may be set as a setting range.

(3d) In the second embodiment, an example case is described in which when the appearing position and the disappearing position are the same, it is determined that the appearing person and the disappearing person are the same person, and it is determined that the driver is not in an abnormal state. However, the method of determining whether the driver is in an abnormal state is not limited to this. For example, when the appearing person appears in the operable range from outside the setting range, that is, outside the operable range, the driver may be determined to be in an abnormal state regardless of the direction in which the person appears.

(3e) In each of the above embodiments, the abnormality determination system 100 may be mounted on a vehicle other than a bus.

(3f) A function of one configuration element in the embodiments described above may be implemented by multiple configuration elements. Functions of multiple configuration elements may be implemented by one configuration element. A part of the configuration according to the embodiments described above may be omitted. At least a part of the configuration of the above embodiments may be added to, replaced with another configuration of the above embodiment, or the like.

(3g) The present disclosure may be implemented in various forms, in addition to the abnormality determination apparatus 2 described above, such as a system including the abnormality determination apparatus 2 as a component, a program for causing a computer to function as the abnormality determination apparatus 2, a medium in which the program is stored, and an abnormality determination method.

For reference to further explain features of the present disclosure, the description is added as follows.

A vehicle control apparatus executes appropriate processing for safety when the vehicle driver is in an abnormal state that interferes with driving. The vehicle control apparatus determines whether the driver is in a drowsiness state or an inoperable state based on the driver's state monitoring information and the driver's face information detected in the captured image by the camera. If it is determined that the driver is in a drowsiness state or an inoperable state, the vehicle control such as deceleration and stop is executed.

There are various possible abnormal states of the driver. A detailed study by the inventors has found the following issue. That is, the vehicle control apparatus that determines the abnormal state of the driver based on the information of only the driver as described above fails to detect the abnormal state that does not appear in the face information of the driver. Therefore, the determination of the abnormal state in the driver is not sufficient.

It is thus desired to make it possible to detect an abnormal state of a driver that cannot be detected by information of only the driver.

An aspect of the present disclosure described herein is set forth in the following clauses.

According to an aspect of the present disclosure, an abnormality determination apparatus mounted on a vehicle is provided to include an identification unit, a person determination unit, and an abnormality processing unit. The identification unit is configured to identify a person in a captured image acquired from a camera that captures a range including a driver seat of the vehicle. The person determination unit is configured to determine whether a person other than the driver of the vehicle is present in an operable range set as a range in which a steering wheel of the vehicle is enabled to be operated, based on an identification result by the identification unit. The abnormality processing unit executes an abnormality process assuming that the driver of the vehicle is in an abnormal state in response to the person determination unit determining that the person other than the driver is present in the operable range.

With such a configuration, it is possible to detect an abnormal state of the driver that cannot be detected by the information of the driver only. That is, for example, when a passenger perceives an abnormal state of a driver in a bus or the like, the passenger may intervene in steering operation. In such a case, a passenger other than the driver is present in the operable range. Therefore, even if the abnormal state of the driver cannot be detected by the information of only the driver, it is determined that a person other than the driver is present in the operable range, and therefore the abnormal process is executed.

What is claimed is:

1. An abnormality determination apparatus mounted on a vehicle, comprising:
   an identification unit configured to identify a person in a captured image acquired from a camera that captures an image of a range including a driver seat of the vehicle;
   a person determination unit configured to determine whether two or more persons are present in an operable range set as a range in which a steering wheel of the vehicle is enabled to be operated based on an identification result by the identification unit; and
   an abnormality processing unit configured to execute an abnormality process assuming that the driver is in an abnormal state in response to the person determination unit determining that two or more persons are present in the operable range and to execute the abnormality process based on (i) a disappearing position where a person disappears from the operable range and (ii) an appearing position where a person appears in the operable range.

2. The abnormality determination apparatus according to claim 1, wherein:
   the identification unit is further configured to recognize a human face in the captured image;
   the person determination unit is configured to determine whether a person other than the driver is present in the operable range based on the recognition result by the identification unit; and
   the abnormality processing unit is configured to execute the abnormality process in response to the person determination unit determining that the person other than the driver is present in the operable range.

3. The abnormality determination apparatus according to claim 1, further comprising:
   a presence determination unit configured to determine whether a person is present in the operable range based on the identification result by the identification unit,
   wherein:
   each of the disappearing position and the appearing position is classified into one of two positions of a left position and a right position with respect to the driver seat; and
   in cases that a person appears in the operable range after the presence determination unit determines that no person is present in the operable range, the abnormality processing unit is configured
      to execute the abnormality process in response to the appearing position and the immediately preceding disappearing position being different from each other, and
      not to execute the abnormality process in response to the appearing position and the immediately preceding disappearing position being same.

4. The abnormality determination apparatus according to claim 3, wherein:
   in response to a state in which no person appears in the operable range continuing for a predetermined period of time or longer after the presence determination unit determines that no person is present in the operable range, the abnormality process is executed by the abnormality processing unit.

5. The abnormality determination apparatus according to claim 1, further comprising:
   a controller circuit coupled via a communication link with the camera, the controller circuit being configured to implement the identification unit, the person determination unit, and the abnormality processing unit.

6. An abnormality determination apparatus mounted on a vehicle, comprising:
   an identification unit configured to identify a person in a captured image acquired from a camera that captures an image of a range including a driver seat of the vehicle;
   a person determination unit configured to determine whether a passenger who is a person other than a driver of the vehicle is present in an operable range set as a range in which a steering wheel of the vehicle is enabled to be operated based on an identification result by the identification unit; and
   an abnormality processing unit configured to execute an abnormality process assuming that the driver is in an abnormal state in response to the person determination unit determining that the passenger is present in the operable range, wherein:

the person determination unit determines whether two or more persons are present in the operable range based on the identification result by the identification unit;

the person determination unit is configured to determine that the passenger is present in the operable range in response to determining that two or more persons are present; and the abnormality processing unit is configured to execute the abnormality process based on (i) a disappearing position where a person disappears from the operable range and (ii) an appearing position where a person appears in the operable range.

7. The abnormality determination apparatus according to claim 6, wherein:

the identification unit is further configured to recognize a human face in the captured image; and the person determination unit is configured to determine whether the passenger is present in the operable range based on the recognition result by the identification unit.

8. The abnormality determination apparatus according to claim 6, further comprising:

a presence determination unit configured to determine whether a person is present in the operable range based on the identification result by the identification unit, wherein:

each of the disappearing position and the appearing position is classified into one of two positions of a left position and a right position with respect to the driver seat; and in cases that a person appears in the operable range after the presence determination unit determines that no person is present in the operable range, the abnormality processing unit is configured to execute the abnormality process in response to the appearing position and the immediately preceding disappearing position being different from each other, and not to execute the abnormality process in response to the appearing position and the immediately preceding disappearing position being same.

9. The abnormality determination apparatus according to claim 8, wherein:

in response to a state in which no person appears in the operable range continuing for a predetermined period of time or longer after the presence determination unit determines that no person is present in the operable range, the abnormality process is executed by the abnormality processing unit.

10. The abnormality determination apparatus according to claim 6, further comprising:

a controller circuit coupled via a communication link with the camera, the controller circuit being configured to implement the identification unit, the person determination unit, and the abnormality processing unit.

11. An abnormality determination apparatus mounted on a vehicle, comprising:

a controller circuit coupled via a communication link with a camera that captures an image of a range including a driver seat of the vehicle, the controller circuit being configured to identify a person in a captured image acquired from the camera to provide an identification result, to determine whether two or more persons are present in an operable range set as a range in which a steering wheel of the vehicle is enabled to be operated based on the identification result, to execute an abnormality process assuming that the driver is in an abnormal state in response to determining that two or more persons are present in the operable range, and to execute the abnormality process based on (i) a disappearing position where a person disappears from the operable range and (ii) an appearing position where a person appears in the operable range.

12. The abnormality determination apparatus according to claim 11, wherein:

the controller circuit is further configured to recognize a human face in the captured image to provide a recognition result, to determine whether a person other than the driver is present in the operable range based on the recognition result, and to execute the abnormality process in response to determining that the person other than the driver is present in the operable range.

\* \* \* \* \*